Figure 1B:
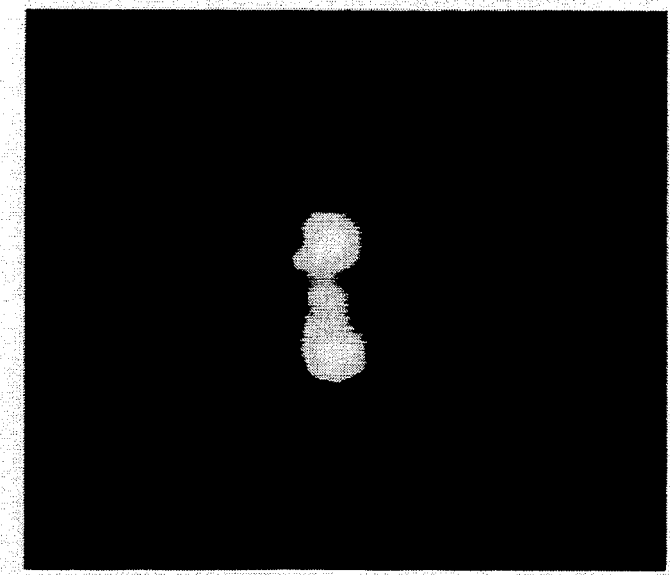

United States Patent [19]

Kuhar et al.

[11] Patent Number: 5,413,779
[45] Date of Patent: * May 9, 1995

[54] COCAINE RECEPTOR BINDING LIGANDS

[75] Inventors: Michael J. Kuhar, Baltimore, Md.; Frank I. Carroll, Durham, N.C.; John W. Boja, Baltimore, Md.; Anita H. Lewin, Chapel Hill; Philip Abraham, Cary, both of N.C.

[73] Assignees: Research Triangle Institute, Research Triangle Park, N.C.; The United States of America represented by the Secretary of Health and Human Services, Washington, D.C.

[ * ] Notice: The portion of the term of this patent subsequent to Jul. 7, 2009 has been disclaimed.

[21] Appl. No.: 972,472
[22] PCT Filed: Aug. 9, 1991
[86] PCT No.: PCT/US91/05553
§ 371 Date: Mar. 23, 1993
§ 102(e) Date: Mar. 23, 1993
[87] PCT Pub. No.: WO92/02260
PCT Pub. Date: Feb. 20, 1992

Related U.S. Application Data

[63] Continuation-in-part of Ser. No. 564,755, Aug. 9, 1990, Pat. No. 5,128,118.

[51] Int. Cl.[6] .................... A61K 49/02; C07D 451/02
[52] U.S. Cl. .................... 424/1.85; 546/132
[58] Field of Search .................... 424/1.45, 1.85; 546/124, 132, 4, 10

[56] References Cited

U.S. PATENT DOCUMENTS

| | | | |
|---|---|---|---|
| 3,813,404 | 5/1924 | Clarke et al. | 546/132 |
| 4,041,040 | 8/1977 | Christenson et al. | 424/1.1 X |
| 4,179,567 | 12/1979 | Clarke et al. | 546/132 |
| 4,366,154 | 12/1992 | Tomesch | 546/132 |
| 5,128,118 | 7/1992 | Carroll et al. | 424/1.1 |
| 5,262,428 | 11/1993 | Davies et al. | 546/124 |
| 5,288,872 | 2/1994 | Davies et al. | 546/132 |
| 5,310,912 | 5/1994 | Neumeyer et al. | 546/132 |

OTHER PUBLICATIONS

Life Sciences, vol. 46, No. 9, pp. 635–645, 1990, M. C. Ritz, et al., "Cocaine Inhibition of Ligand Binding at Dopamine, Norepinephrine and Serotonin Transporters: A Structure–Activity Study".

Journal Of Medicinal Chemistry, vol. 16, No. 11, pp. 1260–1267, 1973, Robert L. Clarke, et al., "Compounds Affecting the Central Nervous System. 4.3 Beta–Phenyltropane-2-Carboxylic Esters and Analogs".

The Journal of Medicinal Chemistry, vol. 33, No. 7, pp. 2024–2027, Jul. 1990, R. H. Kline Jr., et al., "Synthesis of 3-Arylecgonine Analogues as Inhibitors of Cocaine Binding and Dopamine Uptake".

The Journal Of Neuroscience, vol. 9, No. 8, pp. 2664–2670, Aug. 1989, D. E. Grigoriadis, et al., "Dopamine Transport Sites Selectively Labeled by a Novel Photoaffinity Probe: 125I-Deep".

European Journal Of Pharmacology, vol. 200, No. 2–3, pp. 369–370, Aug. 6, 1991, R. Innis, et al., "Single Photon Emission Computed Tomography Imaging of Monoamine Reuptake Sites in Primate Brain with [123I]Cit".

(List continued on next page.)

*Primary Examiner*—Richard D. Lovering
*Assistant Examiner*—John M. Covert
*Attorney, Agent, or Firm*—Oblon, Spivak, McClelland, Maier, & Neudstadt

[57] ABSTRACT

3β-[4-iodophenyl]-tropan-2β-carboxylic acid methyl ester tartrate is a high affinity binding ligand for cocaine receptors in mammalian brains. It and its congeners may be employed for imaging and other brain scanning techniques that allow the determination of the presence of cocaine receptors, such as dopamine and serotonin transporters and the like.

17 Claims, 1 Drawing Sheet

OTHER PUBLICATIONS

European Journal Of Pharmacology, vol. 194, No. 1, pp. 133–134, Feb. 26, 1991, J. W. Boja, et al., "[125I]RTI-55: A Potent Ligand for Dopamine Transporters".

Journal Of Medicinal Chemistry, vol. 34, No. 9, Sep. 1991, pp. 2719–2725, F. I. Carroll, et al., "Synthesis, Ligand Binding, Qsar, and CoMFA Study of 3β-(-p-substituted phenyl) Tropane, 2β Carboxylic Acid Methyl Esters".

Journal of Medicinal Chemistry, vol. 34, No. 10, Oct. 1991, pp. 3144–3146, J. L. Neumeyer, et al., "[123I]-2-β-Carbomethoxy-3β-(4 Iodophenyl) Tropane: High-Affinity Spect Radiotracer of Monoamine Reuptake Sites in Brain".

Chemical Abstract 112(1):539p.

Molecular Pharmacology, vol. 36, No. 4, 1989, (USA); Madras et al.: "Cocaine Receptors Labeled by [3H]2.β.-Carbomethoxy-3.β.-(4-Fluorophenyl) Tropane", pp. 518–524.

COCAINE RECEPTOR BINDING LIGANDS

This application is a continuation-in-part of U.S. application Ser. No. 07/564,755, filed Aug. 9, 1990, now U.S. Pat. No. 5,128,118.

TECHNICAL FIELD

This invention is directed to a binding ligand for cocaine and other receptors in the brain. Specifically, a novel family of compounds, represented by 3β-[4-iodophenyl]-tropan-2β-carboxylic acid methyl ester (RTI-55) tartrate shows high binding specificity and activity, and, in a radiolabeled form, can be used to bind these receptors, for biochemical or imaging techniques.

BACKGROUND ART

Continuing attempts to understand, diagnose, treat and prevent neural disorders rely, in part, on localization or imaging techniques, allowing researchers to determine the location, number and size of specific neurological phenomena. Among those sites undergoing specific testing are cocaine receptors associated with dopamine and serotonin transporter sites.

In order to be useful as a binding ligand for these types of imaging techniques, the compound must have a high affinity for the receptors in question. One such example is the tritiated compound [³H]WIN 35,428, discussed in conjunction with the protocol for determining the relative affinity in binding ligands set forth in the presentation of Carroll et al, 19th Annual FASEB Meeting, Washington, D.C. (1990) incorporated herein-by-reference. Compounds exhibiting high affinity have previously been demonstrated to be useful as binding ligands, in in vitro and in vivo processes. Madras et al, *Molecular Pharmacology*, 36, 518–524 (1989) and Scheffel et al, *Synapse*, 4, 390–394 (1989) both incorporated by reference.

In processes of this type, a radioactively labeled, or similarly labeled compound is administered or injected, depending on in vivo or in vitro processing, and allowed to bind to the transporter sites in question. Thereafter, those sites actually bound to can be determined, by radiographic imaging techniques and the like. In one example, diagnosis of Parkinson's disease may be accomplished by administering a binding ligand having a high affinity for dopamine transporters, and subsequently subjecting the brain to SPECT scanning. The relative frequency of bound sites and imaging obtained allows an assessment of the presence or absence of Parkinson's disease.

Many radioactively labeled ligands, such as the tritiated compound discussed above, or other tritiated or carbon-14 labeled compounds lack sufficient specific activity or affinity are subject to specimen quenching and absorption. Additionally, ideal radiolabeled binding ligands should be useful in powerful scanning and imaging techniques, such as SPECT (Single Photon Emission Computed Tomography) scanning and the like. Thus, improved binding ligands exhibiting these advantages continue to be an object of those of skill in the art.

DISCLOSURE OF THE INVENTION

The family of compounds having the following structure:

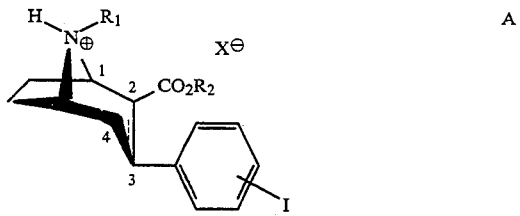

wherein $R_1 = (CH_2)_n CH_3$, n=0–6; $CH_2 CR_3 = CR_4 R_5$ ($R_3$, $R_4$, $R_5$ are all, independently, $C_1$–$C_6$ alkyl); $(CH_2)_y C_6 H_5$, y=1–6;

$R_2 = CH_3$, $C_2 H_5$, $CH_3(CH_2)_3$, $(CH_3)_2 CH$, $C_6 H_5$, $C_6 H_5 CH_2$, $C_6 H_5 (CH_2)_z$, z=1–6;

X = pharmacologically acceptable anion.

of which 3β-[4-iodophenyl]-tropan-2β-carboxylic acid methyl ester (RTI-55) tartrate is an example have been demonstrated to have a high affinity for binding to cocaine receptors, among them the dopamine transporters in the brain. Additionally, RTI-55 has been demonstrated to have an extremely high affinity for another cocaine receptor, serotonin transporters. As this class of compounds bears an iodine atom, this atom can be substituted with a radioactive isotope, such as I-125, I-123 or I-131. Iodinated compounds of this type have advantages over prior art tritiated or carbon-14 labeled compounds. Notably, the high specific activity, reduced specimen quenching and absorption, and susceptibility for use in SPECT scanning and the like, offers advantages not found in prior art compounds. Additionally, these compounds are much easier to make.

3β-[4-iodophenyl]-tropan-2β-carboxylic acid methyl ester (RTI-55) is an exemplary ligand, and the invention is discussed below in terms of this compound. Compound (1) is nitrated with nitrosonium tetrafluoroborate in acetonitrile, to give p-nitro derivative (2) see Chart I. Catalytic hydrogenation of this derivative, using a Raney nickel catalyst, converts the nitro group, to an aminated intermediate 3. Diazotization, in the presence of methylene iodide, gives the compound of this invention. Alternatively, compounds like 3β-(trimethyltinphenyl)-tropan-2β-carboxylic acid ester (4) obtained by treating bromo or iodo analogs of A with hexamethylditin in the presence of a suitable catalyst can be used as intermediates. These intermediates can be converted to radioactive I-labeled compounds of the invention ($^{123}$I or $^{125}$I) by treatment with iodine of the desired isotope.

Studies showing the high affinity of this compound for cocaine receptors such as dopamine and serotonin transporters and other cocaine receptors have been conducted, demonstrating the utility of the invention.

Figure 1A:

BRIEF DESCRIPTION OF FIG. 1(a) AND (b)

A comparison of CT and SPECT images on baboon nervous tissue is presented in the drawing, as indicated.

BEST MODE FOR CARRYING OUT THE INVENTION

3β-[4-iodophenyl]-tropan-2β-carboxylic acid methyl ester (RTI-55) tartrate is synthesized according to the process outlined in Chart I. Nitration of 3β-(phenyl)tropan-2-carboxylic acid methyl ester (1) with nitrosonium tetrafluoroborate in acetonitrile gives the p-nitro compound 2. Catalytic hydrogenation of 2 using Raney nickel as catalyst afforded the p-amino compound 3. Diazotization of 3 in the presence of methylene iodide followed by treatment with tartaric acid gives the exemplary compound of the invention. The parameters of the process steps, per se, are well known, and familiar to those of ordinary skill in the art. These reaction mechanisms, per se, do not constitute an aspect of the invention.

The obtained salt has a melting point of 72°–74° C. It has a high solubility in conventional solvents including water, acid, base, methanol, ethanol and acetone solvents. The compounds of the invention are relatively insoluble in chloroform, ether, petroleum ethers and benzene and not stable with respect to heat or light.

phosphine) palladium (0) (see Scheme). Since treatment of 4 with iodine gives RTI-55, it follows that treatment of 4 with $^{125}I_2$ and $^{123}I_2$ will provide the I-125 and I-123 analogs [$^{125}I$]-RTI-55 and [$^{123}I$]-RTI-55, respectively.

3β-(4-trimethyltinphenyl)-tropan-2β-carboxylic acid methyl ester (4). A mixture of hexamethylditin (440 mg, 1.33 mmol), 3β-(4-iodophenyl)-tropan-2β-carboxylic acid methyl ester (RTI-55) (385 mg, 1.0 mmol) and palladium-tetrakis-triphenylphosphine (5 mg catalytic amount) in dry toluene (30 mL) was heated under reflux under a nitrogen atmosphere for 5 h. The catalyst was removed by filtration, and the combined filtrate and

CHART I:

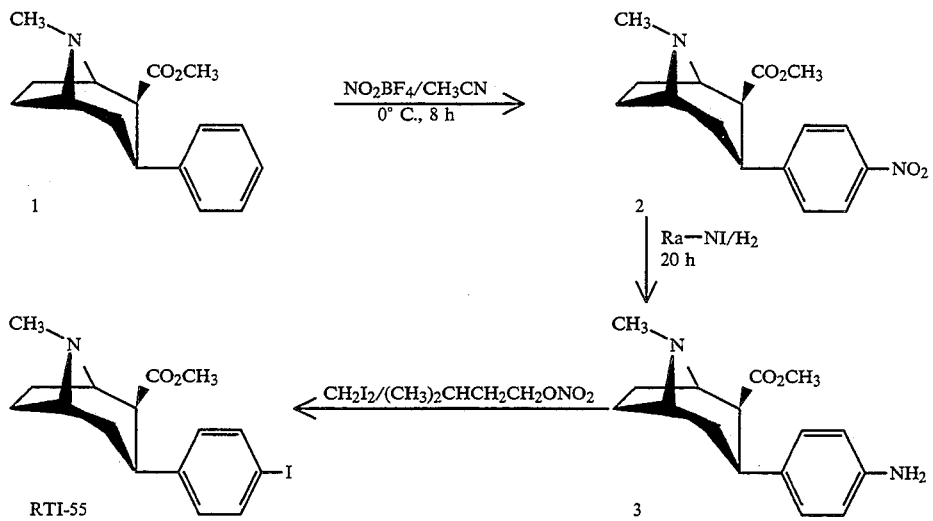

In an alternative within this invention is a preferred synthesis route where 3β-(trimethyltinphenyl)-tropan-2β-carboxylic acid esters are relied on as useful intermediates in the preparation of I-125 or I-123 analogs of compound A. These compounds can be prepared by treating the corresponding 4-bromo or 4-iodo analogs with hexamethylditin catalyzed by palladium (0). This is described by the scheme set forth below in Chart II.

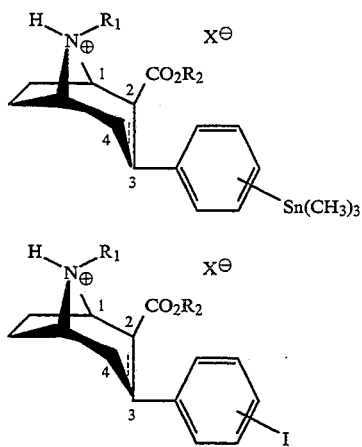

3β-(4-trimethyltin)tropan-2β-carboxylic acid methyl ester (4) was prepared by treating 3β-(p-iodophenyl)-tropan-2β-carboxylic acid methyl ester (RTI-55) with hexamethylditin in the presence of tetrakis(triphenylwashings were evaporated. The residue was purified on a silica gel column eluting with a mixture of hexane:ether:triethylamine (10:9:1) to give 315 mg. This material was rechromatographed on a silica gel column eluting with $CHCl_3:CH_3OH$ (95:5) to give 306 mg (72%) of pure 4 as a colorless oil which crystallized: mp 113°–114°C.; $^1H$ NMR (250 MHz, $CDCl_3$) δ 0.24 [s, 9H, $Sn(CH_3)_3$], 1.60–1.73 (m, 4H, 2H-6, 2H-7), 2.11–2.19 (m, 1H, H-4 endo), 2.33 (s, 3H, $NCH_3$), 2.59 (m, 1H, H-2), 2.91 (m, 2H, H-4 exo, H-3), 3.38 (s, 3H, $OCH_3$), 3.55 (m, 1H, H-1), 7.26–7.38 (ABq, 4H, $C_6H_4$); $[α]_D^{23}+1.6°$ (c, 1, $CHCl_3$).

Anal. Calcd for $C_{19}H_{29}NO_2Sn$: C, 54.06; H, 6.92, N, 3.32. Found: C, 53.91; H, 7.00; N, 3.29.

3β-(4-iodophenyl)-tropan-2β-carboxylic acid methyl ester (RTI-55). To a stirred suspension of 3β-(4-trimethyltinphenyl)-tropan-2β-carboxylic acid methyl ester (4) (26 mg, 0.061 mmol) and K1 (12 mg, 0.072 mmol) in sodium acetate buffer (0.1N AcOH, 0.22N NaOAc, 2 mL) was added chloramine-T (3 mg, catalytic amount) at room temperature. After 45 min, the reaction mixture was basified with $NH_4OH$ (6 N) and extracted with $CH_2Cl_2$ (5×5 mL). The combined extracts were dried ($Na_2SO_4$) and evaporated. The residue was purified on a silica gel column. Eluting with a mixture of hexane:ether:triethylamine (50:45:5) gave RTI-55 (18 mg, 76%) as a waxy solid. The residue was dissolved in pentane, evaporated to dryness and kept under vacuum to give RTI-55 a white powder: mp 101°–102° C. The $^1H$ NMR spectrum was identical to that of authentic RTI-55.

CHART II:

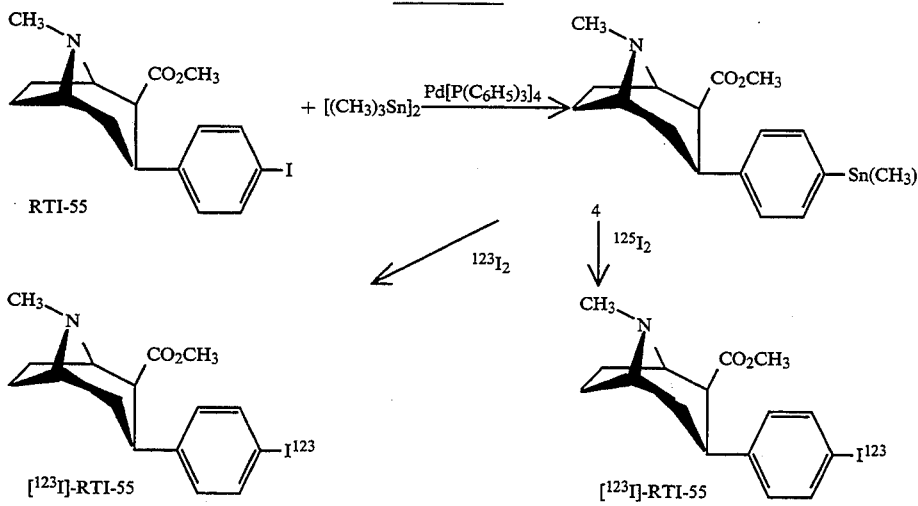

3β-[4-iodophenyl]-tropan-2β-carboxylic acid methyl ester (RTI-55) tartrate has been demonstrated to have a high relative affinity for dopamine transporters. Affinity was determined according to the protocol of Carroll et al, discussed above. Using this protocol, various other prior art binding ligands, [$^3$H]WIN 35,428 for example, are co-incubated with various concentrations of the binding ligand to be measured, in 0.5 nM [$^3$H]WIN 35,428 in 10 nM phosphate buffer, pH 7.4, containing 0.32M sucrose. The reaction is allowed to proceed for two hours, at which time the reaction is terminated. The bound radioactivity is measured. The relative affinity for various binding ligands at the dopamine transporter site, determined according to this protocol, is set forth below, in terms of the IC$_{50}$ value obtained in Table 1. Relative affinity values for various binding ligands at the serotonin transporter sites are given in Table 2.

TABLE 1

Inhibition of 0.15 nM [$^{125}$I]RTI-55 binding in rat striatum by various dopamine reuptake inhibitors. Values are the means ± SE of 3–5 independent experiments performed in triplicate.

| | IC$_{50}$ (nM) |
|---|---|
| Cocaine Congeners | |
| (−) Cocaine | 62.50 ± 5.01 |
| (±) Cocaine | 7987.72 ± 576.56 |
| WIN 35,065-2 | 20.41 ± 4.47 |
| WIN 35,065-3 | 840.74 ± 10.54 |
| Dimethocaine | 460.74 ± 18.41 |
| WIN 35,981 | 25.16 ± 3.64 |
| WIN 35,428 | 12.49 ± 1.69 |
| RTI-55 | 0.60 ± 0.05 |
| Non-Cocaine Congeners | |
| Buproprion | 178.39 ± 18.14 |
| Amfonelic Acid | 160.08 ± 17.79 |
| Methylphenidate | 91.26 ± 3.66 |
| Nomifensine | 56.26 ± 13.47 |
| Mazindol | 8.70 ± 0.86 |
| GBR 12909 | 0.79 ± 0.01 |

IC$_{50}$ values reflect potency or affinity at the dopamine transporter. Smaller numbers indicate higher affinity. The inhibitory properties shown here indicate that compound RTI-55 is binding to the dopamine transporter in the striatum.

TABLE 2

Inhibition of 0.15 nM [$^{125}$I]RTI-55 binding in rat cerebral cortex by various compounds.

| | IC$_{50}$ (nM) |
|---|---|
| Dopamine Reuptake Inhibitors | |
| Dimethocaine | 34572.33 ± 150.15 |
| Nomifensine | 1067.58 ± 150.15 |
| (−) Cocaine | 60.61 ± 8.06 |
| Mazindol | 45.08 ± 1.12 |
| WIN 35,428 | 23.70 ± 2.04 |
| GBR 12909 | 3.93 ± 0.52 |
| Norepinephrine Reuptake Inhibitors | |
| Desipramine | 649.12 ± 56.43 |
| Nisoxetine | 635.70 ± 105.69 |
| 5-Hydroxytryptamine Reuptake Inhibitors | |
| Imipramine | 62.69 ± 1.88 |
| Clomipramine | 2.05 ± 0.26 |
| Citalopram | 0.49 ± 0.08 |
| Sertaline | 0.30 ± 0.05 |
| 5-HT Receptor Antagonists | |
| Methyseride | 34842.37 ± 4504.56 |
| Cinnanserine | 1986.74 ± 46.09 |
| Metergoline | 595.07 ± 14.86 |
| Ketanserine | 307.67 ± 30.05 |

Values for IC$_{50}$ were calculated using EBDA (computer software for sampling determination) and are the means ± SE of 3–5 independent experiments performed in triplicate. The pharmacological data shown here indicate that [$^{125}$I]RTI-55 binds to serotonin transporters in rat cerebral cortex.

While the above shows that [$^{125}$I]RTI-55 has a high affinity for both dopamine and serotonin transporters in vitro, we have also found that [$^{125}$I]RTI-55 is a useful in vivo binding ligand. Compounds that are useful as in vitro labeling ligands are not necessarily reliably predicted, on that basis, as useful in vivo labeling ligands. But data from our laboratory show that, after systemic administration in rodents and sub-human primates, radiolabeled RTI-55 preferentially binds to dopamine transporters and serotonin transporters. The data include regional localization as well as pharmacological findings. These data are represented in part by the figure attached hereto. The figure shows a CT scan on the left and a SPECT scan of [$^{123}$I]RTI-55 on the right. A baboon was injected with [$^{123}$I]RTI-55 and the baboon was subjected to CT and SPECT scans. On the right, it can be seen that after intravenous administration,

[$^{123}$I]RTI-55 accumulates in the basal ganglia, a region containing high densities of dopamine transporters (the purpose of the CT scan is to aid in the identification of the basal ganglia). This indicates the usefulness of RTI55 as a SPECT imaging agent for dopamine transporters. Under other conditions it can be shown that RTI-55 binds to serotonin transporters as well.

Because radiolabeled RTI-55 binds preferentially to both serotonin and dopamine transporters in vivo, it can be used as an imaging agent for both PET and SPECT scanning. PET (Positron Emission Tomography) scanning may require the carbon 11 labeled form of the drug, while SPECT scanning may use the I-123 labeled form of the drug. It could be used in the following ways.

A. To examine the density and distribution of certain cocaine receptors in various parts of the body.

B. To compare these densities in normal and disease states and use observed changes that can be associated with diseases as indicators diagnostic of diseased states. For example, in Parkinson's disease, there is a degeneration of dopaminergic nerve terminals in basal ganglia; the degeneration of these nerve terminals result in a loss of dopamine transporters in this region and this loss could be detected by imaging dopaminergic transporters. The invention may also be employed to determine progression of the disease and/or prognosis as to various treatment regimens.

Also, another example would be a situation where there is degeneration of specific nerves in brain due to various toxins; some drugs of abuse, such as substituted amphetamines, cause a degeneration of serotonin-containing nerve terminals. Since the serotonin transporter is a selective marker for serotonergic nerve terminals, imaging serotonin transporters would be a useful approach in serotonin-containing systems in brain.

C. To screen for drugs that would have a high affinity at serotonin transporters or dopamine transporters. Serotonin transporters are important in that they are a target for antidepressant drugs. This ligand could be used in screening studies to identify potentially new useful antidepressant drugs. Also, there are various compounds and environmental toxins that may destroy nerve terminals after being transported into the nerve terminal. Substituted amphetamines are mentioned above in this regard. This ligand could be used in screening studies to identify compounds that could be transported by or into various nerve terminals and be neurotoxic.

Additionally, this compound may be used in the treatment of drug abusers. It has been suggested that high affinity ligands are capable of special utility in treating drug abusers (Rothman, R.B. *Life Sci.* 46:17–21, 1990. It is also possible that this substance could be used in substitution therapy, much as methadone is used to treat heroin addiction.

A brief description of an imaging procedure is as follows:

Tracer quantities of the radioactive iodine labeled ligand will be injected intravenously into subjects positioned in a SPECT scanner. After injection of the compound, the scanner will be turned on to begin to collect data. The ligand will preferentially localize to dopamine transporters over about one hour, with the best localization perhaps occurring at about 30–50 minutes. The time period for localization to serotonin transporters may be marginally less. The amount of compound bound will reflect the density of transporters. The target of these experiments will be the basal ganglia where the dopamine transporters are concentrated. Disease states such as Parkinson's disease will show a reduction in transporter density.

Obviously, modifications and variations of the present invention are possible in light of the above teachings. In particular, various synthesis parameters, as well as scanning methodologies and the like may be employed, as alternatives to the exemplification set forth. It is therefore to be understood that within the scope of the appended claims, the invention may be practiced otherwise than as specifically described herein.

We claim:

1. A compound of the formula below,
where the broken line represents an optional chemical bond;
the iodo substituent may be at o, m, p, or multisubstituted and is a radioactive isotope;
$R_1 = (CH_2)_n CH_3$, n=0–6; $CH_2CR_3 = CR_4R_5$ ($R_3$, $R_4$, $R_5$ are each, independently, $C_1$–$C_6$ alkyl); $(CH_2)_y C_6H_5$ (y=1–6);
$R_2 = CH_3$, $C_2H_5$, $CH_3(CH_2)_3$, $(CH_3)_2CH$, $C_6C_5$, $C_6H_5CH_2$, $C_6H_5(CH_2)_z$ (z=1–6); and
X = pharmacologically acceptable anion.

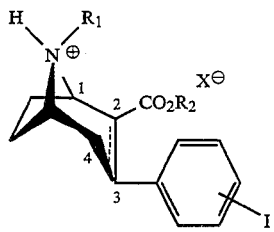

2. The compound of claim 1, wherein said radioactive isotope is $^{123}$I.

3. The compound of claim 1, wherein said radioactive isotope is $^{131}$I.

4. The compound of claim 1, wherein said iodine moiety is in the para position.

5. The compound of claim 1, wherein at least one carbon atom thereof is $^{11}$C.

6. The compound of claim 1, wherein said radioactive isotope is $^{125}$I.

7. A compound of the formula

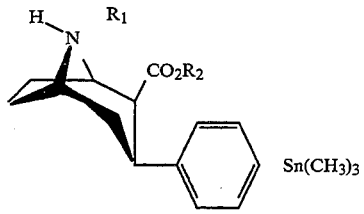

wherein $Sn(CH_3)_3$ is ortho, meta or para, or multisubstituted and
$R_1 = (CH_2)_n CH_3$ (n=0–6); $CH_2CR_2 = CR_4R_5$ ($R_3$, $R_4$, $R_5$ are each independently $C_1$–$C_6$ alkyl); $(CH_2)_y C_6H_5$ (y=1–6);
$R_2 = CH_3$, $C_2H_5$, $CH_3(CH_2)_3$, $(CH_3)_2CH$, $C_6H_5$, $C_6H_5CH_2$, $C_6H_5(CH_2)_z$ (z=1–6).

8. A method of assaying for the presence of cocaine receptors in the brain of a mammal, comprising administering a compound of claim 1 in a biologically acceptable carrier to said mammal, allowing said radioactively labeled compound to bind to cocaine receptors in the brain of said mammal, and scanning the brain of said mammal to determine the presence of radioactive iodine bound thereto, wherein the presence of radioactive iodine corresponds to a cocaine receptor site.

9. The process of claim 8, wherein said receptor is a dopamine receptor.

10. The process of claim 8, wherein said radioactive iodine isotope is $^{125}I$, $^{123}I$ or $^{131}I$.

11. The process of claim 10, wherein said radioactive iodine isotope is $^{125}I$.

12. The process of claim 10, wherein said radioactive iodine isotope is $^{123}I$.

13. A method of determining density and distribution of brain receptors in a patient, comprising administering an amount effective to effectuate binding to said receptors of the radioactively labeled compound of claim 1, in a pharmaceutically acceptable carrier, permitting said compound to bind to said receptors, and obtaining an image of the distribution and density of the compounds so bound.

14. The method of claim 13, wherein said compound is labeled with $^{123}I$.

15. The method of claim 13, wherein said compound is labeled with $^{131}I$.

16. A method for screening potential central nervous system-affecting drugs, comprising:
administering a potential CNS-affecting drug to a mammal in an amount effective to provide for binding of said drug to cocaine receptors in said mammal, administering a compound of claim 1 to said mammal in amounts effective to provide for binding of said compound to cocaine receptors in said mammal, obtaining an image of the compound so bound, and comparing said image against a control image of the binding of said compound to said cocaine receptors in the absence of said drug.

17. A method of screening chemicals for neurotoxicity, comprising:
administering a suspect neurotoxic chemical to a mammal in an amount effective to provide for interaction between nerve terminals in said mammal and said chemical, administering a compound of claim 1 to said mammal in amounts effective to provide for binding of said compound to cocaine receptors of said mammal, obtaining an image of the compound so bound, and comparing said image against a control image of the binding of said compound in the absence of said chemical.

* * * * *

UNITED STATES PATENT AND TRADEMARK OFFICE
CERTIFICATE OF CORRECTION

PATENT NO. : 5,413,779
DATED : May 9, 1995
INVENTOR(S) : Michael J. Kuhar, et al.

It is certified that error appears in the above-indentified patent and that said Letters Patent is hereby corrected as shown below:

Column 1, line 57, after affinity, please insert --and--.

Column 8, lines 47-57, the chemical structure should appear as follows:

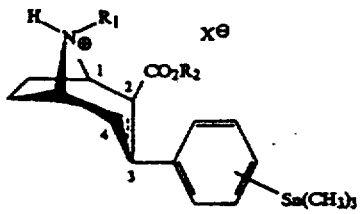

Column 8, line 60, $CH_2CR_2=CR_4R_5$ should read --$CH_2CR_3=CR_4R_5$--.

Column 9, line 8, please delete receptor and insert therefore --transporter--.

Signed and Sealed this

Thirteenth Day of August, 1996

Attest:

BRUCE LEHMAN

Attesting Officer        Commissioner of Patents and Trademarks